(12) United States Patent
Wada et al.

(10) Patent No.: US 9,345,393 B2
(45) Date of Patent: May 24, 2016

(54) ENDOSCOPE CAMERA

(71) Applicant: PANASONIC CORPORATION, Osaka (JP)

(72) Inventors: Jyouji Wada, Kanagawa (JP); Yuuichi Takenaga, Fukuoka (JP); Masahiko Misawa, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 236 days.

(21) Appl. No.: 13/788,345

(22) Filed: Mar. 7, 2013

(65) Prior Publication Data
US 2013/0242071 A1 Sep. 19, 2013

(30) Foreign Application Priority Data

Mar. 13, 2012 (JP) ................................. 2012-055832

(51) Int. Cl.
*A61B 1/05* (2006.01)
*A61B 1/04* (2006.01)
*A61B 1/00* (2006.01)
*G02B 23/24* (2006.01)

(52) U.S. Cl.
CPC ................. *A61B 1/05* (2013.01); *A61B 1/0008* (2013.01); *A61B 1/00183* (2013.01); *A61B 1/041* (2013.01); *G02B 23/2484* (2013.01)

(58) Field of Classification Search
CPC .................... H04N 2005/2255; H04N 5/2253; H04N 5/23203; A61B 1/05; A61B 1/0607
USPC .......................................................... 348/76
See application file for complete search history.

(56) References Cited

U.S. PATENT DOCUMENTS

| 7,959,563 | B2 | 6/2011 | Fukuhori | |
|---|---|---|---|---|
| 2004/0027459 | A1* | 2/2004 | Segawa | A61B 1/0011 348/207.99 |
| 2005/0043586 | A1* | 2/2005 | Suzushima | 600/160 |
| 2006/0244822 | A1* | 11/2006 | Konno | H04N 5/2251 348/77 |
| 2007/0038215 | A1* | 2/2007 | Hahn | A61B 18/149 606/46 |
| 2007/0191683 | A1* | 8/2007 | Fujimori | A61B 1/041 600/173 |
| 2008/0021281 | A1* | 1/2008 | Fujimori | A61B 1/00016 600/160 |
| 2008/0045798 | A1* | 2/2008 | Fukuhori | A61B 1/041 600/175 |
| 2008/0081947 | A1* | 4/2008 | Irion | A61B 1/00183 600/109 |

(Continued)

FOREIGN PATENT DOCUMENTS

| EP | 2082680 | 7/2009 |
|---|---|---|
| JP | 07-327916 | 12/1995 |

(Continued)

OTHER PUBLICATIONS

EP Search Report dated Jun. 18, 2013.

*Primary Examiner* — Sath V Perungavoor
*Assistant Examiner* — Howard D Brown, Jr.
(74) *Attorney, Agent, or Firm* — Greenblum & Bernstein, P.L.C.

(57) ABSTRACT

There is provided an endoscope camera that achieves closer cumulative tolerance of a camera head and achieves improved accuracy in positioning the camera head. An endoscope camera includes a cylindrical hard case, a camera head provided at a distal end portion of the hard case, and a cover attached to the distal end portion of the hard case which covers the camera head. A rib wall having a holding section is provided inside the cover, and an abutment section which is held by the holding section is provided at the camera head. The abutment section is biased toward the holding section.

9 Claims, 9 Drawing Sheets

(56) References Cited

U.S. PATENT DOCUMENTS

| | | | |
|---|---|---|---|
| 2009/0018398 A1* | 1/2009 | Segawa | A61B 1/041 600/178 |
| 2009/0052059 A1* | 2/2009 | Lin | A61B 1/00096 359/755 |
| 2009/0244259 A1* | 10/2009 | Kojima | H04N 5/2251 348/45 |
| 2009/0281374 A1* | 11/2009 | Leanna | A61B 1/00087 600/101 |
| 2009/0287048 A1* | 11/2009 | Jacobson et al. | 600/109 |
| 2010/0010312 A1* | 1/2010 | Gilad | A61B 1/00167 600/160 |

FOREIGN PATENT DOCUMENTS

| | | |
|---|---|---|
| JP | 2001/137182 | 5/2001 |
| JP | 2005/205072 | 8/2005 |
| JP | 2006/230680 | 9/2006 |
| JP | 2008-043626 | 2/2008 |

\* cited by examiner

ENDOSCOPE CAMERA

BACKGROUND OF THE INVENTION

1. Field of the Invention

The present invention relates to an endoscope camera having improved camera head positioning accuracy.

2. Description of the Related Art

Hard endoscope cameras have been used in various fields, such as medical and industrial fields. Such an endoscope camera is required to have the function of changing the direction of the field of view of the endoscope camera according to the intended use and an object to be observed. A conventional endoscope camera is thus provided with a mechanism for changing the imaging direction of an image pickup section (the direction of the field of view of the endoscope camera) according to the intended use and an object to be observed. Recent advances in the performance of endoscope cameras have complicated drive mechanisms for endoscope cameras and have created a demand for extremely high camera head positioning accuracy.

For example, such a hard endoscope camera is disclosed in Japanese Patent Laid-Open No. 7-327916.

However, in conventional endoscope cameras, the position of a cover relative to a camera head is determined by the cover and a hard case. Especially an endoscope camera with an elongated hard case has looser cumulative tolerance when a camera head is mounted and has lower accuracy in positioning a spherical center of a cover and an optical axis of the camera head relative to each other, which causes the problem of image quality degradation.

SUMMARY OF THE INVENTION

The present invention has been made to solve the above-described conventional problem and has an object to provide an endoscope camera that achieves closer cumulative tolerance of a camera head and achieves improved accuracy in positioning the camera head.

An endoscope camera according to the present invention includes a cylindrical hard case, a camera head provided at a distal end portion of the hard case, and a dome-shaped cover attached to the distal end portion of the hard case which covers the camera head. The cover is provided with a holding section, the camera head is provided with an abutment section, and the abutment section is held by the holding section to locate a spherical center of the cover on an optical axis of the camera head.

This configuration achieves closer cumulative tolerance between the camera head and the cover and achieves improved accuracy in positioning the camera head and the cover relative to each other.

In the endoscope camera according to the present invention, the abutment section is biased toward the holding section.

This configuration achieves closer cumulative tolerance between the camera head and the cover and achieves improved accuracy in positioning the camera head and the cover relative to each other.

In the endoscope camera according to the present invention, the cover is provided with a rib wall for reinforcing the cover.

This configuration allows maintenance of the strength of the cover even in a case where the cover is a thin dome-shaped cover.

In the endoscope camera according to the present invention, the rib wall is provided with the holding section.

This configuration allows maintenance of the strength of the dome-shaped cover with a simple structure and achieves improved accuracy in positioning the camera head and the cover relative to each other.

In the endoscope camera according to the present invention, a first space for housing the camera head and a second space for housing an illumination section are formed inside the cover, and the rib wall intervenes between the first space and the second space.

With this configuration, the rib wall between the first space (a space for housing the camera head) and the second space (a space for housing the illumination section) can inhibit light (illumination light or reflected light of illumination light) from the illumination section from entering the camera and can reduce the occurrence of flare.

The endoscope camera according to the present invention further includes a rotation drive section which rotates the camera head about a rotation axis of the camera head and a bearing member which pivotally supports the camera head such that the camera head is rotatable about the rotation axis. The abutment section comprises a distal end portion of the bearing member.

This configuration allows use of the distal end portion of the bearing member of the camera head as the abutment section.

In the endoscope camera according to the present invention, the abutment section comprises a shaft member which is provided on the rotation axis of the camera head.

This configuration allows use of the shaft member of the camera head as the abutment section.

The present invention can provide an endoscope camera which achieves closer cumulative tolerance of a camera head and achieves improved accuracy in positioning the camera head.

DETAILED DESCRIPTION OF THE PREFERRED EMBODIMENTS

An endoscope apparatus according to an embodiment of the present invention will be described below with reference to the drawings. The present embodiment will be described in the context of a medical endoscope camera which is used as a laparoscope or the like for observing the interior of the abdomen.

Figure 1:
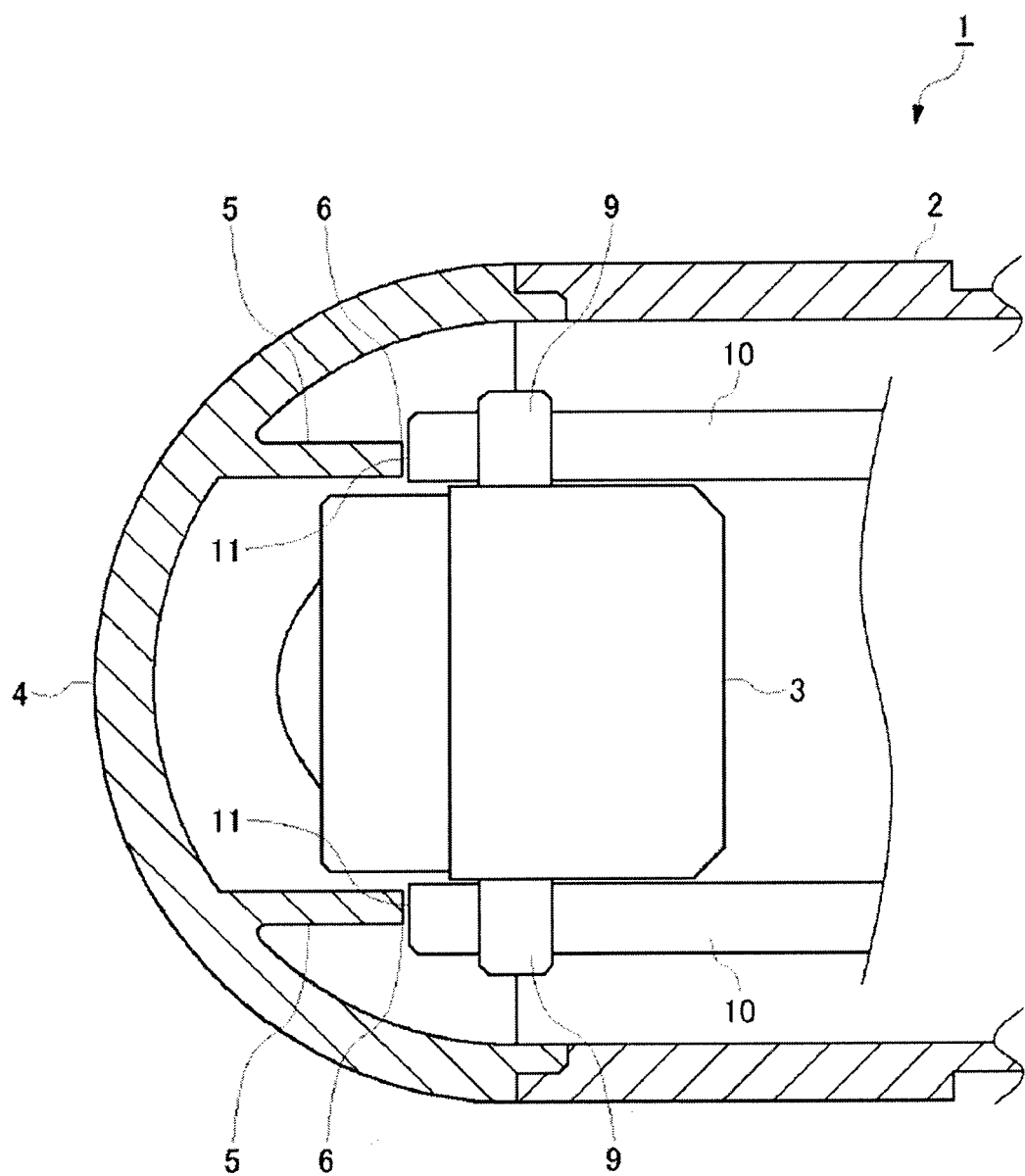
FIG. 1 is a plan view of an endoscope camera according to an embodiment of the present invention.
Figure 2:
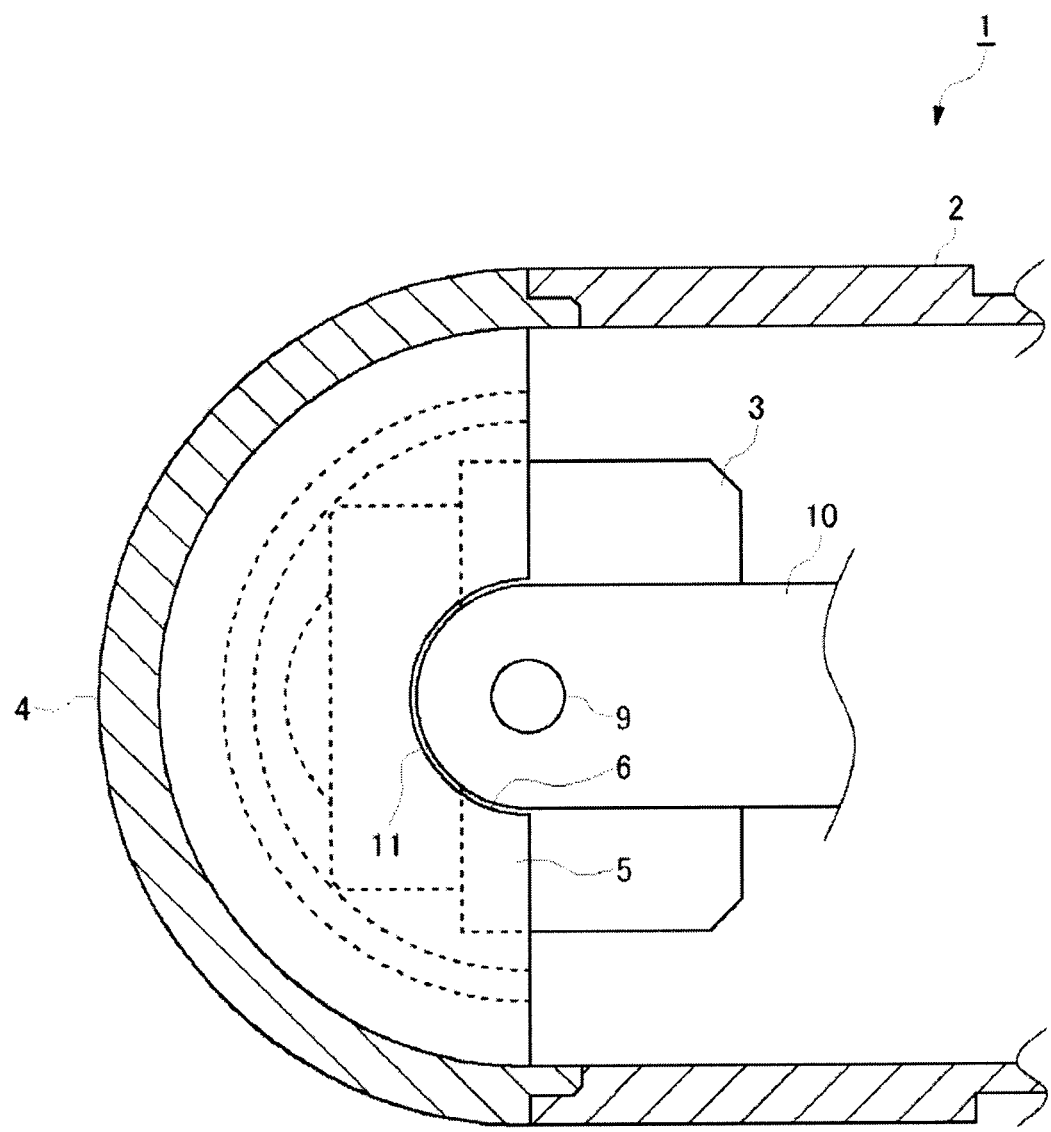
FIG. 2 is a side view of the endoscope camera according to the embodiment of the present invention.
Figure 3:
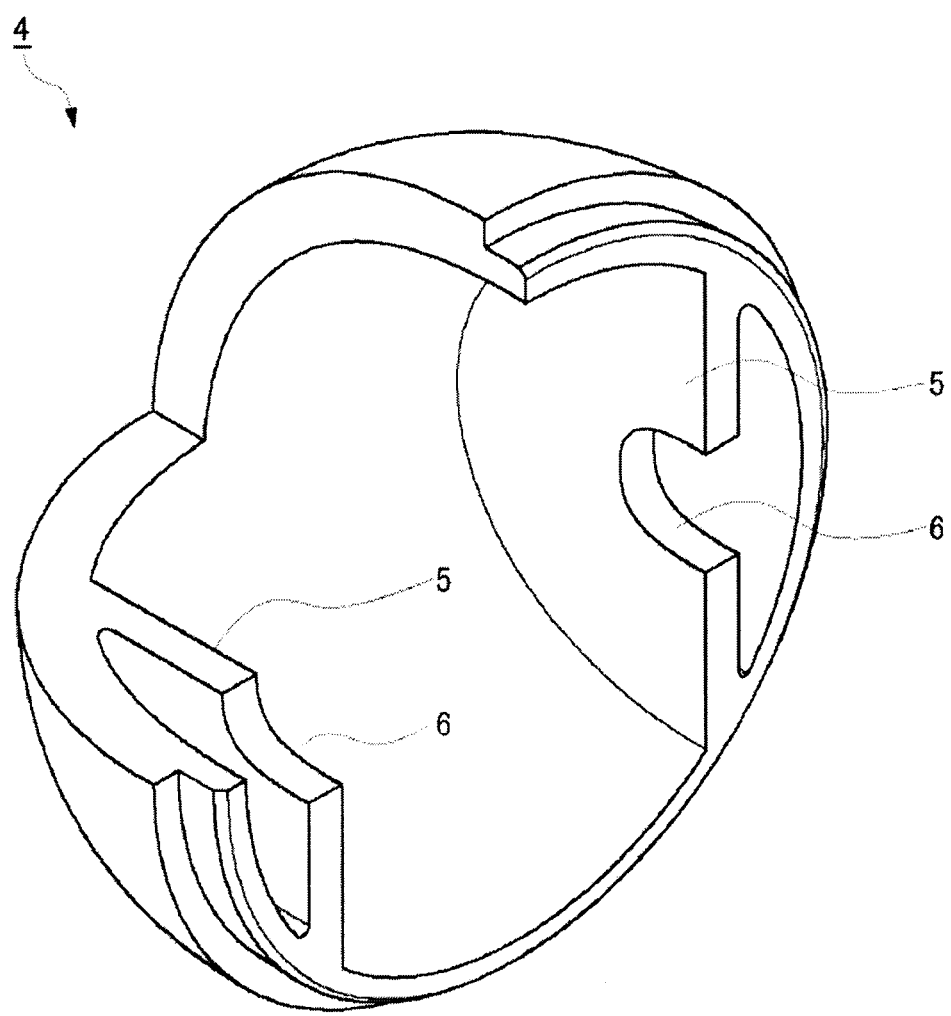
FIG. 3 is a perspective view of a cover of the endoscope camera according to the embodiment of the present invention.
Figure 4:
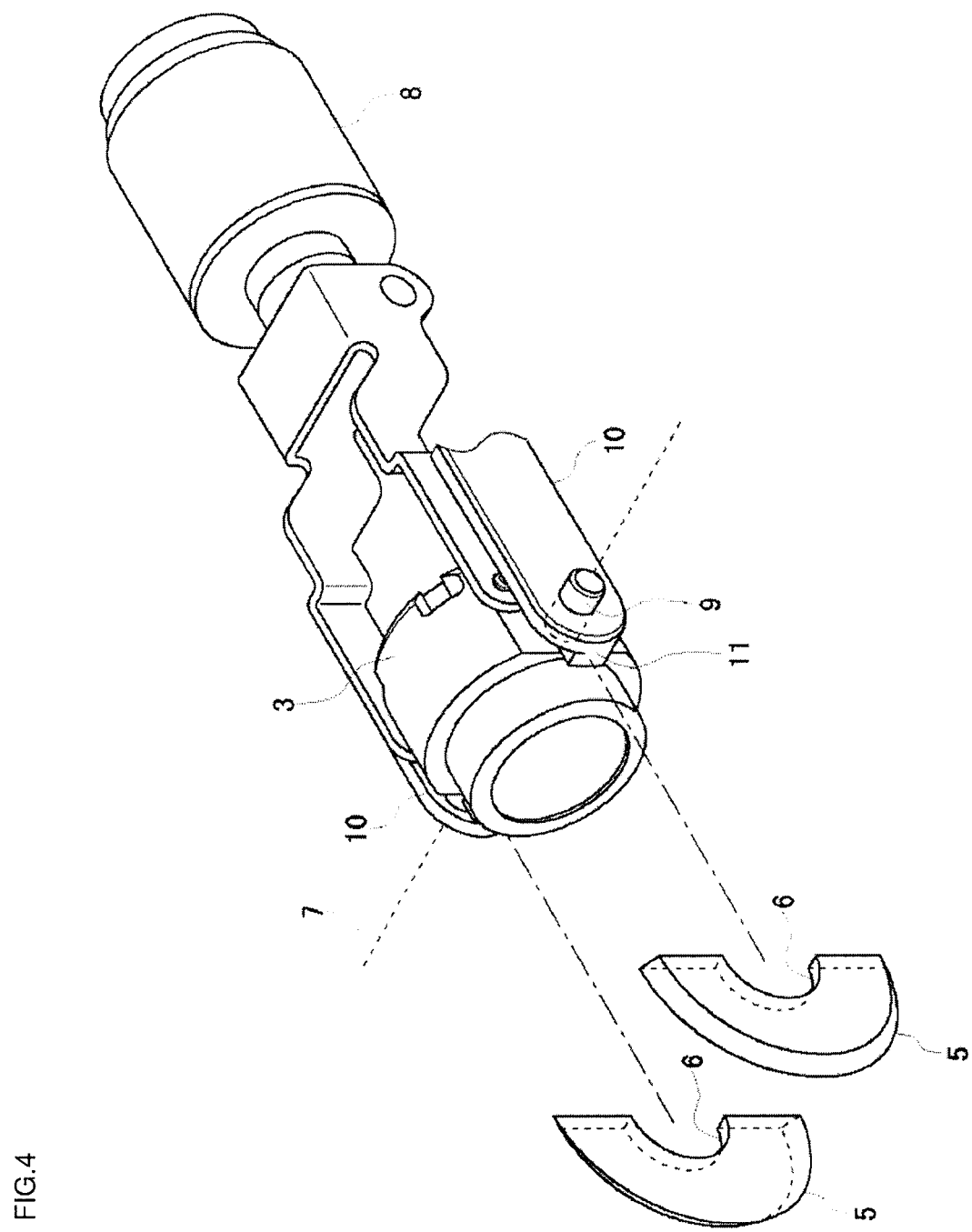
FIG. 4 is a perspective view of a main configuration of the endoscope camera according to the embodiment of the present invention.

The configuration of an endoscope camera according to the embodiment of the present invention will be described with reference to FIGS. 1 to 4. FIG. 1 is a plan view of the endoscope camera, and FIG. 2 is a side view of the endoscope camera. FIG. 3 is a perspective view of a cover of the endoscope camera, and FIG. 4 is a perspective view of a main configuration of the endoscope camera. Note that, for convenience of illustration, a part of the cover is cut away in FIG. 3 and only a part (rib walls) of the cover is shown in FIG. 4.

As shown in FIGS. 1 to 4, an endoscope camera 1 according to the present embodiment includes a cylindrical hard case 2 and a camera head 3 which is provided at a distal end portion of the hard case 2. A hemispherical (dome-shaped) cover 4 which covers an exposed portion of the camera head 3 is attached to the distal end portion of the hard case 2. A pair of left and right substantially semi-circular rib walls 5 is provided inside the cover 4. A substantially semi-circular concave holding section 6 is provided at the center of each rib wall 5. The rib walls 5 are provided substantially parallel to a direction of rotation of a tilt axis.

The camera head 3 is rotatable about a tilt axis 7, and a tilt motor 8 for rotating the camera head 3 in a tilt direction is provided inside the hard case 2. The camera head 3 has a shaft member 9 on the tilt axis 7, and the shaft member 9 is pivotally supported by bearing members 10. Substantially semi-circular convex abutment sections 11 are formed at respective distal end portions of the bearing members 10.

The shape (substantially semi-circular convex shape) of each abutment section 11 corresponds to the shape (substantially semi-circular concave shape) of each holding section 6. The abutment sections 11 are held by the holding sections 6. Here, the abutment sections 11 are biased toward the holding sections 6 by biasing means (not shown) such as a spring.

The endoscope camera 1 according to the embodiment described thus far achieves closer cumulative tolerance of the camera head 3 and achieves improved accuracy in positioning the camera head 3.

In the present embodiment, the abutment sections 11 provided at the camera head 3 are held by the holding sections 6 provided at the rib walls 5 of the cover 4 and are biased toward the holding sections 6. The abutment sections 11 at the camera head 3 and the holding sections 6 at the cover 4 are provided such that a spherical center of the semi-spherical (dome-shaped) cover 4 is located on an optical axis of the camera head 3. Especially since the abutment sections 11 are provided at the bearing members 10 that hold the camera head 3 via the shaft member 9, error in the positional relationship between the optical axis of the camera head 3 and the abutment sections 11 can be minimized. The holding sections 6 of the cover 4 are integral with the cover 4, and error in the positional relationship between the holding sections 6 and the spherical center of the cover 4 can also be minimized.

The above-described configuration achieves closer cumulative tolerance between the camera head 3 and the cover 4 and achieves improved accuracy in positioning the camera head 3 and the cover 4 relative to each other. In this case, the distal end portions of the bearing members 10 of the camera head 3 can be used as the abutment sections 11.

Note that if the camera head 3 is rotated in the tilt direction, the positional relationship may be such that the spherical center of the cover 4 is located at the intersection of the optical axis of the camera head 3 and the tilt axis of the camera head 3. In the case of a fixed camera having the non-rotatable camera head 3, image quality degradation caused by the cover 4 can be prevented as long as the spherical center of the cover 4 is on the optical axis of the camera head 3. Note that the spherical center of the cover 4 need not coincide exactly with the optical axis and may deviate slightly to the extent not degrading camera image quality.

Since the cover 4 is provided with the rib walls 5, the strength of the cover 4 can be secured even if a spherical surface portion of the cover 4 is thin. Especially in the case of a small camera such as an endoscope camera ($\Phi$=10.5 mm), if the cover 4 has a large thickness, an image may be degraded by the lens effect due to the small radius of the spherical surface of the cover 4. The dome-shaped cover 4 thus desirably has a small thickness. The holding sections 6 and abutment sections 11 can be firmly coupled by bonding them together. This prevents the cover 4 from being removed and improves the reliability of the endoscope camera used inside the body.

Additionally, a large gate can be provided at a portion corresponding to a rib wall at the time of molding. This improves the flow of resin and improves the optical characteristics of a light transmissive portion.

First Modification

Figure 5:
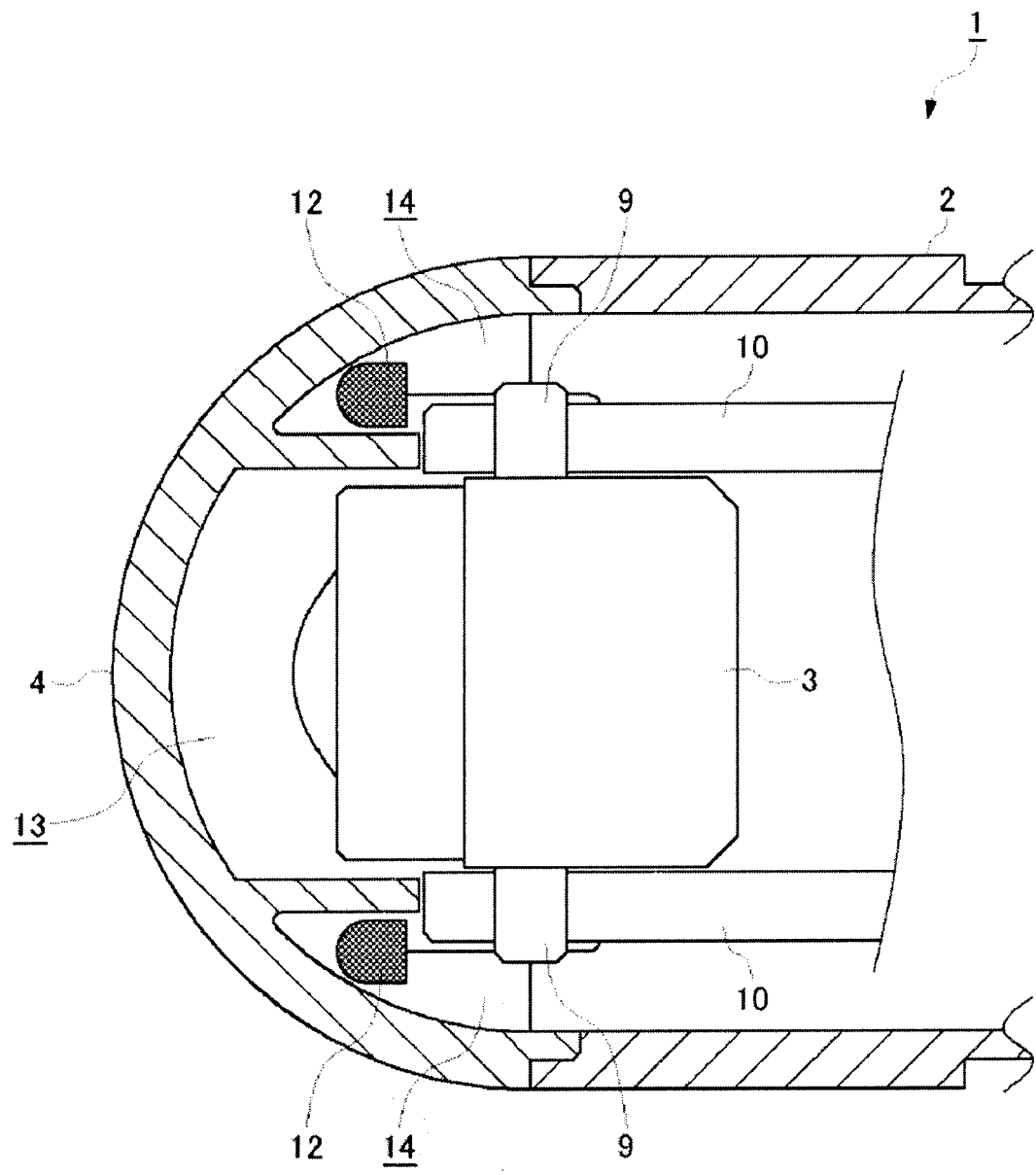
FIG. 5 is a plan view of the endoscope camera (a first modification) according to the embodiment of the present invention.

FIG. 5 shows a first modification of the endoscope camera 1. As shown in FIG. 5, in the endoscope camera 1 according to the first modification, illumination sections 12 such as an LED are housed in a space inside the cover 4 which is partitioned with the rib walls 5. It can also be said that a space (a first space 13) for housing the camera head 3 and spaces (second spaces 14) for housing the respective illumination sections 12 are formed inside the cover 4 and that the rib walls 5 intervene between the first space 13 and the second spaces 14, respectively. Note that the illumination sections 12 may be composed of, e.g., an optical fiber which guides light from external lighting equipment.

The first modification with the above-described configuration has the same working effects as the above-described embodiment. Additionally, the first modification can inhibit light (illumination light or reflected light of illumination light) from each illumination section 12 from entering the camera (for example, by attaching a light-blocking board) and can reduce the occurrence of flare by making an outer surface (the outer side) of each rib wall 5 between the first space 13 (the space for housing the camera head 3) and the second space 14 (the space for housing the illumination section 12) lightproof. Moreover, if an inner surface (the inner side) of each rib wall 5 is made lightproof (for example, by attaching a light-blocking board), light from the outside can be prevented from being reflected on the inner surface of the rib wall 5 to enter the camera.

Second Modification

Figure 6:
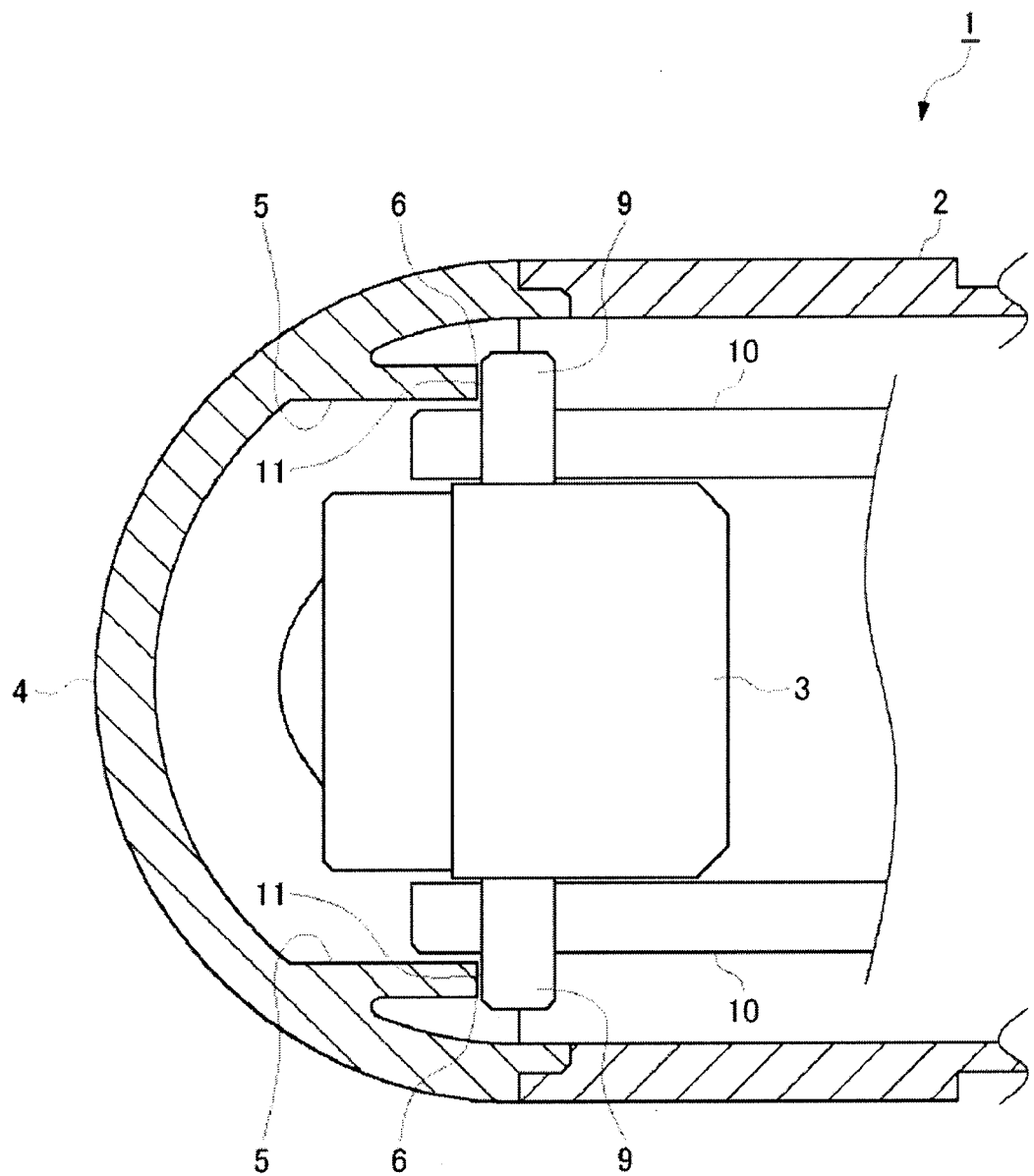
FIG. 6 is a plan view of the endoscope camera (a second modification) according to the embodiment of the present invention.
Figure 7:
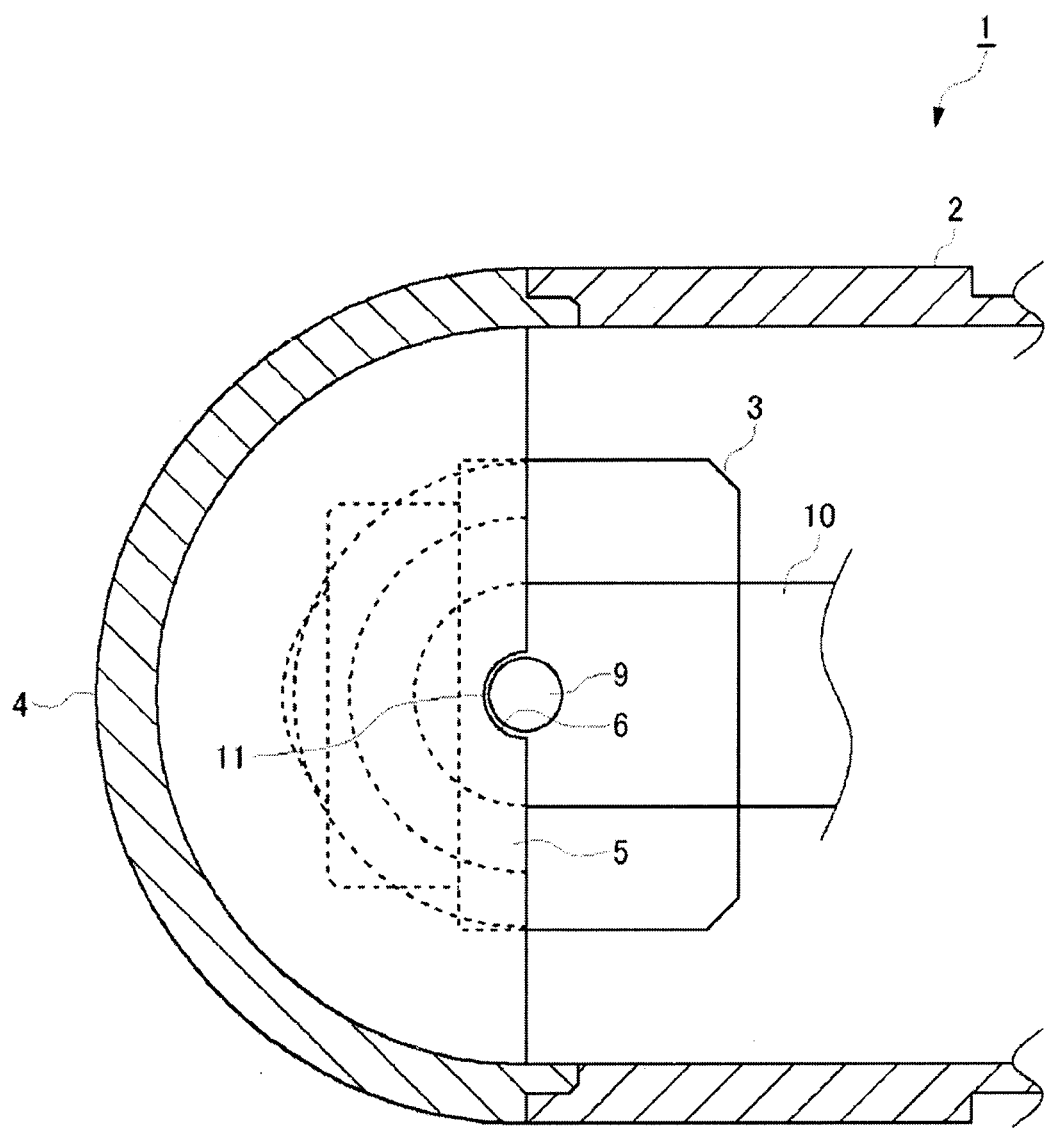
FIG. 7 is a side view of the endoscope camera (the second modification) according to the embodiment of the present invention.

FIGS. 6 and 7 show a second modification of the endoscope camera 1. As shown in FIGS. 6 and 7, in the endoscope camera 1 according to the second modification, the shaft member 9 of the camera head 3 is used as the abutment sections 11. Here, the shape (substantially semi-circular concave shape) of each holding section 6 corresponds to the shape of the shaft member 9.

The second modification with the above-described configuration has the same working effects as the above-described embodiment. In the second modification, the shaft member 9 of the camera head 3 can be used as the abutment sections 11.

Figure 8:
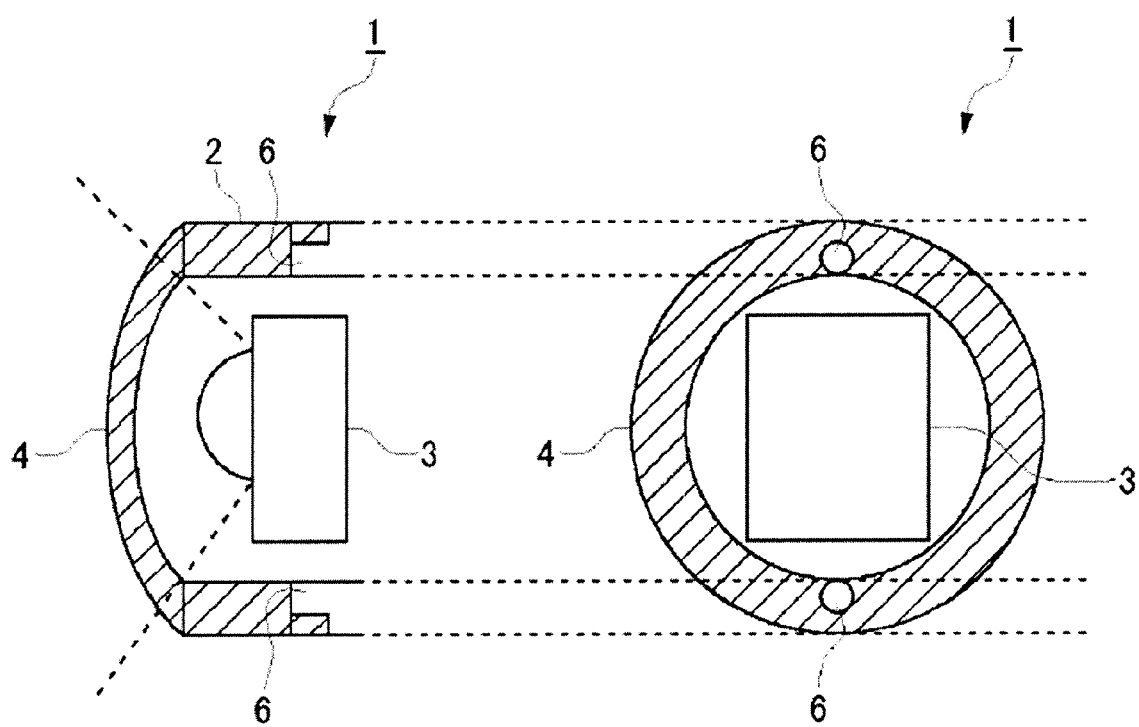
FIG. 8 is a view for explaining another modification of the endoscope camera according to the embodiment of the present invention.
Figure 9:
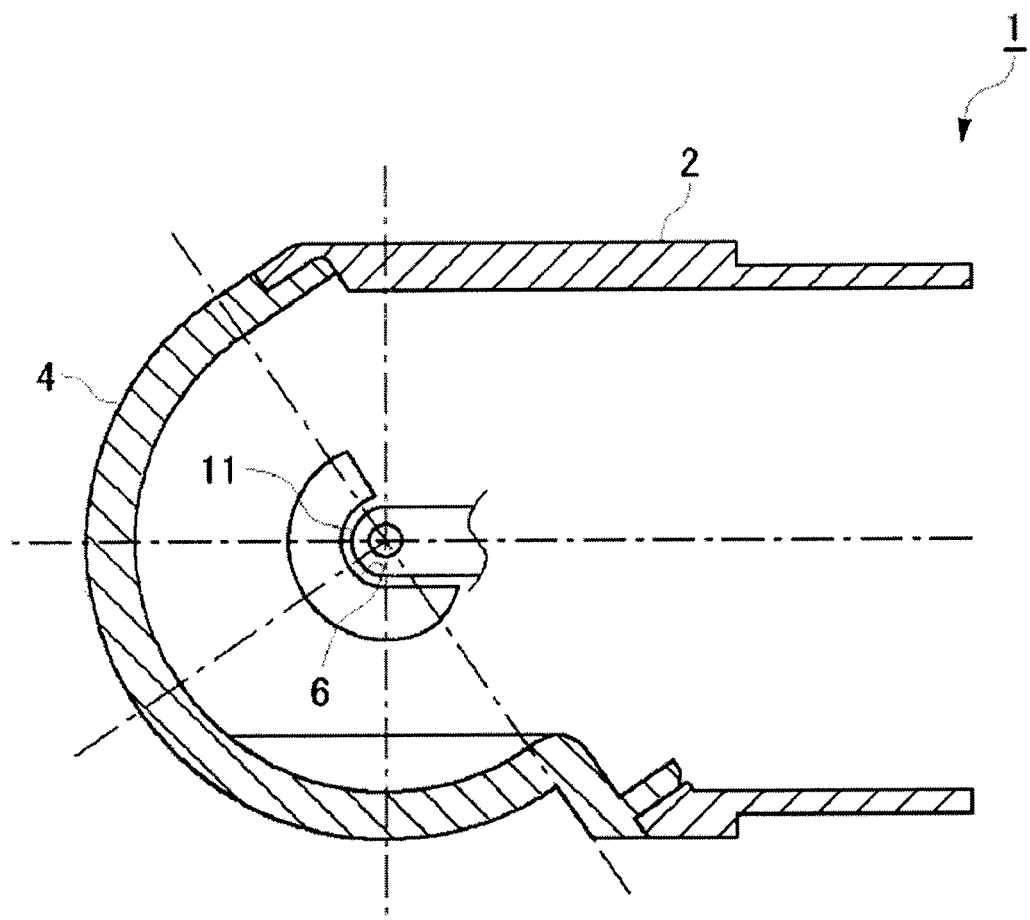
FIG. 9 is a view for explaining still another modification of the endoscope camera according to the embodiment of the present invention.

As shown in FIG. 8, the cover 4 need not be entirely spherical, and only a portion within an imaging area of the camera head 3 needs to be spherical. As shown in FIG. 9, the cover 4 may be attached obliquely relative to the hard case 2.

The embodiment of the present invention has been described above by way of example. The scope of the present invention, however, is not limited to this. Changes and modifications may be made depending on the specific application without departing from the scope of the claims.

As has been described above, an endoscope according to the present invention has the advantages of closer cumulative tolerance of a camera head and improved accuracy in positioning the camera head. The endoscope camera is useful as, e.g., a medical or industrial endoscope camera.

What is claimed is:

1. An endo scope camera comprising:
    a cylindrical hard case;
    a camera head provided at a distal end portion of the hard case; and
    a dome-shaped cover attached to the distal end portion of the hard case which covers the camera head,
    wherein the cover is provided with a holder, the camera head is provided with an abutment, and the abutment is held by the holder to locate a spherical center of the cover on an optical axis of the camera head,
    wherein the cover is provided with a rib wall for reinforcing the cover,
    wherein the holder is provided within the rib wall,
    wherein a first space for housing the camera head and a second space for housing an illuminator are provided inside the cover, and
    wherein the illuminator is disposed between the rib wall and the cover.

2. The endo scope camera according to claim 1, wherein the abutment is biased toward the holder.

3. The endo scope camera according to claim 1, further comprising:
    a rotation driver which rotates the camera head about a rotation axis of the camera head; and
    a bearing member which pivotally supports the camera head such that the camera head is rotatable about the rotation axis,
    wherein the abutment comprises a distal end portion of the bearing member.

4. The endo scope camera according to claim 1, wherein the abutment comprises a shaft member which is provided on the rotation axis of the camera head.

5. The endo scope camera according to claim 1, wherein the rib wall extends from the cover.

6. The endo scope camera according to claim 1,
    wherein the illuminator is disposed on one side of the rib wall, and
    wherein the camera head is disposed on another side of the rib wall.

7. The endo scope camera according to claim 1, wherein the holder comprises an arcuate surface.

8. The endo scope camera according to claim 1, wherein a light-blocking board is provided on a surface of the rib wall.

9. The endoscope camera according to claim 1, wherein the rib wall is provided on an interior surface of the cover.

* * * * *